Figure 1:
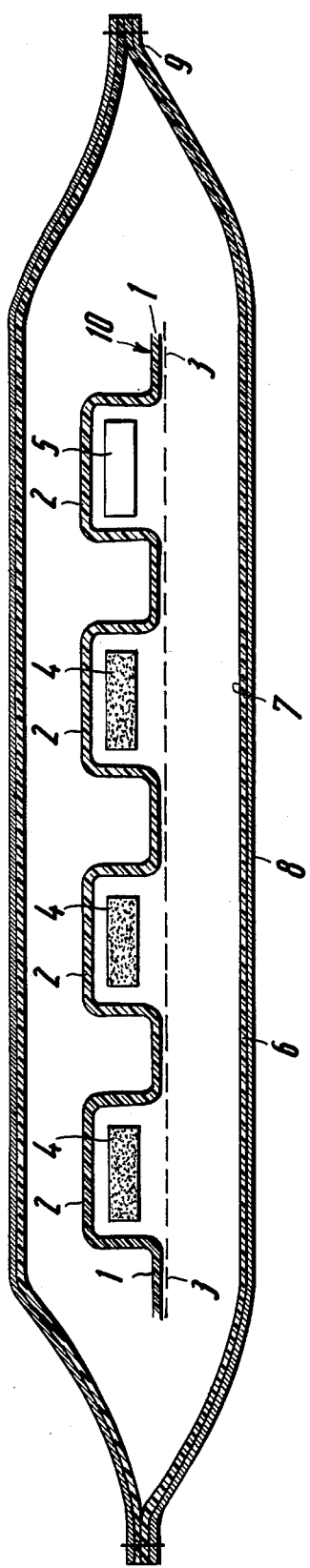

United States Patent [19]

Schoom

[11] 4,039,611
[45] Aug. 2, 1977

[54] METHOD FOR TREATING RESIDUES, LEFT OVER AFTER THE GAS RELEASE, OF PEST CONTROL AGENTS THAT CONTAIN EARTH METAL PHOSPHIDES AND/OR ALKALINE EARTH METAL PHOSPHIDES

[75] Inventor: Werner Schoom, Bergen-Enkheim, Germany

[73] Assignee: Deutsche Gesellschaft fur Schadlingbekampfung, Frankfurt am Main, Germany

[21] Appl. No.: 558,275

[22] Filed: Mar. 14, 1975

Related U.S. Application Data

[63] Continuation of Ser. No. 331,890, Feb. 12, 1973, abandoned.

[30] Foreign Application Priority Data

Feb. 11, 1972 Germany ............................ 2206494

[51] Int. Cl.² .................... C01B 25/00; C01G 1/00

[52] U.S. Cl. ...................................... 423/1; 423/299; 423/659

[58] Field of Search ............................ 423/1, 299, 659

[56] References Cited

U.S. PATENT DOCUMENTS 3,719,751  3/1973  Rauscher et al. .................... 424/27

FOREIGN PATENT DOCUMENTS 538,958  4/1957  Canada ............................... 423/299
651,937  11/1962  Canada ............................... 423/299

OTHER PUBLICATIONS

Chem. Abstracts, vol. 75, (1971), p. 93831h.
Chem. Abstracts, vol. 75, (1971), pp. 128815 k and 128816 m.

Primary Examiner—Edward Stern

[57] ABSTRACT

A water soluble oxidizing material is packaged with gas releasing pest control agents for decomposing residual gas producing agents.

4 Claims, 2 Drawing Figures

METHOD FOR TREATING RESIDUES, LEFT OVER AFTER THE GAS RELEASE, OF PEST CONTROL AGENTS THAT CONTAIN EARTH METAL PHOSPHIDES AND/OR ALKALINE EARTH METAL PHOSPHIDES

This application is a continuation of application Ser. No. 331,890, filed Feb. 12, 1973, which application is now abandoned. The applications are related to co-pending application Ser. No. 331,891, filed Feb. 12, 1973, now U.S. Pat. No. 3,866,347.

For the control of pests, particularly insects and rodents agents are employed that contain as active ingredient earth metal phosphides and/or alkaline earth metal phosphides. They may also contain water-repellent materials, such as hard paraffin, metal stearates, or wax like materials, e.g. polyalcohols, and compounds such as ammonium carbamate or urea, which are decomposed by the effect or heat and/or moisture, while gas is generated. The said agents are used in powder form or as shaped bodies, such as tablets or pellets. Illustrative examples of such metal phosphides which have been found suitable for use as pest control agents are found in co-pending application Ser. No. 9,073, filed Feb. 5, 1970, which matured into U.S. Pat. No. 3,719,751 on Mar. 6, 1973.

When such pest control agents are brought into rooms where parasites are to be killed, phosphoreted hydrogen, i.e. hydrogen phosphide, which acts as poisonous gas, is produced by the reaction of atmospheric moisture with the earth metal phosphides and/or alkaline earth metal phosphides.

This reaction is sometimes incomplete, so that after the gas release residues may be left over which, beside reaction produced oxides and hydroxides of earth metals and/or alkaline earth metals, also contain still small residues of the corresponding phosphides. If such residues remain any longer, they may produce phosphoreted hydrogen i.e. hydrogen phosphide which endangers the surroundings.

Usually such residues are stirred in water and thus rendered harmless.

Closer investigation has shown that even the treatment with water does in some cases not suffice to decompose rapidly and completely the traces of phosphides contained in the residues.

The object of this invention is to produce a method for treating with water the aforementioned residues left over after the gas released, which method is to assure a rapid and complete decomposition of the phosphide traces contained in the residues and also a neutralization of the phosphoreted hydrogen, i.e. hydrogen phosphide, produced in this process.

According to this invention, this is accomplished by adding to the water employed in the treatment a material or material mixture that is soluble in water, has an oxidizing effect, and imparts to the water a pH-value of less than 7.

For greater convenience, it is advisable to use material or material mixtures which are solid before being dissolved in water and exist in powder form, or preferably, as pressed objects. A material particularly suitable for this purpose is calcium hypochlorite in mixture with citric acid. This compound presents the advantage that the solution produced in the method of the invention contains no substances which are undesirable in waste waters.

Other recommendable oxidizing agents are, e.g., chromic acid, mixtures of sodium perborate with citric acid, of potassium percarbonate with citric acid, and of sodium percarbonate with manganates.

To make the use 90 of the method of the invention easier, it is advisable to add a redox indicator to the water employed for the treatment. By a color change the latter indicates when the oxidizing effect of the used materials or material mixtures has been consumed by reaction with phosphide present in the residues, or with the produced phosphoreted hydrogen. In this case, further quantities of the acid and oxidizing materials or material mixtures may be added to the water, so as to complete the reaction.

For greater convenience, it is frequently advisable to employ the materials or material mixtures to be added to the water in measured quantities in packages which are water soluble or permeable to liquid water. Such packages may be e.g., bags of a fine-meshed tissue or texture; they may also consist of porous paper or of water soluble foils of e.g., polyvinyl alcohol, polyethylene oxide, or gelatin. In these bags or packages the materials or material mixtures may be contained in powder form or as shaped bodies, such as tablets or pellets. Packages or bags of different materials may also be used, in which case, e.g., one side consists of a water soluble foil, the other side or porous paper. One side of the packages or bags may also consist of a material insoluble in water, e.g. a foil of polyvinyl chloride or polyethylene. The edges of such packages or bags may be sealed together.

In many cases it is suitable for the pest control agents a form of dispensation of employment which contains, besides the pest control agent, also the materials or material mixtures required for the method of the invention, in which case the access of atmospheric moisture to the pest control agent, and the access of water to the materials or material mixtures of this invention must of course be assured.

Figure 2:
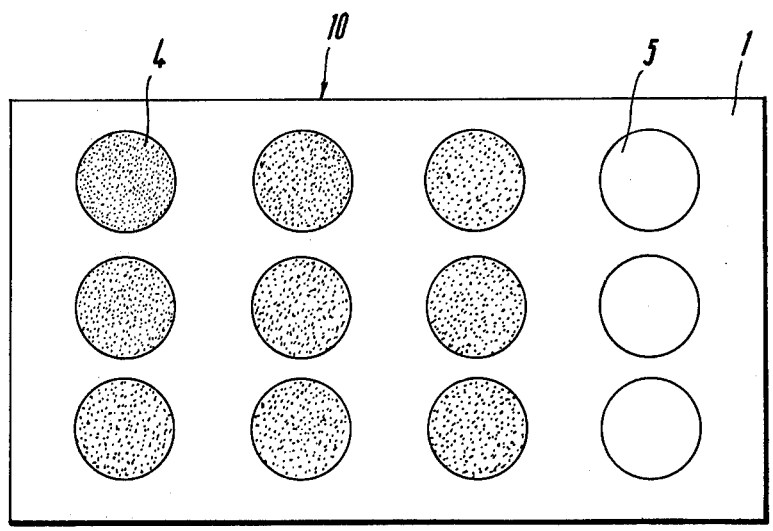

The means by which the objects of this invention are obtained is disclosed more fully with reference to the accompanying drawings, in which:

FIG. 1 is a cross-sectional view through the package containing the pest control and oxidizing materials; and FIG. 2 is a plan view of the materials contained in the package.

In FIG. 1 such a dispensation form is shown in cross-section by way of example. It consists of a thick foil 1 of polyvinyl chloride, in which recesses or burls 2 are made by punching. On the bottom side, a sheet 3 of porous Japanese paper, permeable to water vapor, is provided which is sealed to the foil between the recesses. In the recesses there are tablets 4 of the pest control agent, and tablets 5 consisting of a mixture of calcium hypochloride, citric acid and a small amount of redox indicator.

Both types of tablets 4 and 5 can be mechanically produced and correctly proportioned and are inserted into the recesses or burls 2 before the Japanese paper is sealed on.

When such a dispensation form is brought into a room where the gas is to be released, tablets 4 of the pest control agent decompose, while phosphoreted hydrogen is generated, by the effect of atmospheric moisture which penetrates the foil permeable to gas.

The sizes and amounts of the tablets of pest control agents and the mixture of calcium hypochlorite, citric acid and redox indicator are chosen in such a way that, even if the gas release is incomplete, non-decomposed phosphide is contained no longer in the residues within a very short time after the start of the treatment of the invention, and the phosphoreted hydrogen, i.e. hydrogen phosphide, generated in the process is completely oxidized to harmless compounds.

There are in each bag 6 on foil 1 correctly measured amounts of both tablets 4 and 5, which are adapted to a specific size of the room, e.g., for 10 cubic meter. The dispensation form 10 contained in bag 6 can easily be removed by tearing sealed edges 9 of bag 6 or cutting them off with scissors, and then be deposited in the room where the gas is to be released. The room must then remain closed for a correct period of time, whereby the pests are safely destroyed.

After the gas has been released the entire set is put, e.g., into a bucket with water. Non-decomposed tablets 5 of calcium hypochlorite, citric acid and redox indicator are dissolved in the water. This solution reaches through the pores of the Japanese paper, the residues of tablets 4 of the pest control agent, decomposes the traces of phosphides contained therein and oxidizes the phosphorated hydrogen i.e. hydrogen phosphide, generated in this process to harmless compounds.

For storage and transportation, the entire set is placed in a bag 6 composed of aluminum foil 8 covered with a plastic material 7 so as to be impermeable to gas. The end edges 9 of the bag are sealed gas tight. A plurality of these bags can be placed in a gas tight container composed of metal or plastic.

EXAMPLE

In a closed room with bales of tobacco a dispensation form according to FIG. 1 and 2 was introduced. The foil 1 made of polyvinylchloride comprised 24 recesses or burls 2. 18 of said recesses contained each a tablet of a weight of 3 gm of the following composition:
70% aluminum phosphide
26% amonium carbamate
4% hard paraffine.

The remaining six of the said recesses contained each a tablet, of a weight of 3 gm consisting of
50% calcium hypochlorite and
50% citric acid.

The said room with the bales had a temperature of 30° C and a relative humidity of 90%.

After 24 hours the dispensation form was removed from the room and dumped into a bucket of water.

An examination revealed that the tablets did not contain any longer any traces of aluminum phosphide.

Having now described the means by which the objects of this invention are obtained, I claim:

1. A method of treating the residual remainder of a pest control agent after same has been used the agent containing as an active ingredient a metal phosphide which generates hydrogen phosphide as a toxic gas upon contact with water comprising adding a water-soluble oxidizing agent to a container of water to provide an oxidizing water solution having a pH of below 7, the water being present in an amount sufficient to decompose any remaining unreacted metal phosphide that may be present in the residue, and the oxidizing agent being present in an amount sufficient to oxidize any hydrogen phosphide gas generated by said residue, said oxidizing agent being selected from the group consisting of a mixture of calcium hypochlorite and citric acid, chromic acid, a mixture of sodium perborate and citric acid, a mixture of potassium percarbonate and citric acid and a mixture of sodium percarbonate with manganates, and thereafter adding the pest control agent residue remaining after use to the oxidizing solution and permitting the residue to remain in said oxidizing solution until any unreacted metal phosphide present in the residue has been converted to a completely harmless state.

2. A method in accordance with claim 1, wherein the pest control agent residue and the oxidizing agent are added to the container of water simultaneously.

3. A method in accordance with claim 1, wherein the oxidizing agent is a mixture of 50% by weight of calcium hypochlorite and 50% by weight of citric acid.

4. A method in accordance with claim 1, wherein the active ingredient of the pest control agent is aluminum phosphide and the oxidizing agent is a mixture of 50% by weight of calcium hypochlorite and 50% by weight of citric acid.

* * * * *